United States Patent [19]

Span

[11] Patent Number: 4,836,520
[45] Date of Patent: Jun. 6, 1989

[54] RADIOLOGY PATIENT SUPPORT

[75] Inventor: Francis J. Span, Eindhoven, Netherlands

[73] Assignee: U.S. Philips Corporation, New York, N.Y.

[21] Appl. No.: 133,583

[22] Filed: Dec. 16, 1987

[30] Foreign Application Priority Data

Dec. 19, 1986 [GB] United Kingdom ............... 8630411

[51] Int. Cl.⁴ ............................................. A61G 13/00
[52] U.S. Cl. .................................... 269/322; 269/325
[58] Field of Search ............... 269/322, 323, 324, 325, 269/326, 327

[56] References Cited

U.S. PATENT DOCUMENTS 3,797,819  3/1974  Platz et al. ........................ 269/322
4,589,126  5/1986  Augustsson et al. ............... 378/209
4,657,235  4/1987  Schar ................................ 269/322

FOREIGN PATENT DOCUMENTS 0151910  8/1985  European Pat. Off. .

Primary Examiner—Gene Wan
Attorney, Agent, or Firm—Thomas A. Briody; Jack E. Haken; Jack D. Slobod

[57] ABSTRACT

A radiology patient support system includes a single vertical pillar of rigid closed box construction in which the side walls form a continuous closed cross section which rigidly supports two vertically arranged longitudinal tracks with their lateral directions at a right angle. A vertically displaceable carriage also of rigid box construction, is provided with bearing rollers which respectively engage the tracks and effectively locate the carriage horizontally relative to the pillar. A patent support table top is mounted on the carriage.

9 Claims, 6 Drawing Sheets

RADIOLOGY PATIENT SUPPORT

FIELD OF THE INVENTION

This invention relates to a radiology patient support system for radiography, radiotherapy and treatment simulation, including a fundamental support, a patient support table top mounted on a vertically displaceable carriage, and box section vertical supporting pillar means mounted on the fundamental support and provided with guide means and lifting means arranged to support, locate and vertically displace the vertically displaceable carriage.

A patient support of the kind specified is disclosed for example in European patent application No. 151910 which corresponds to U.S. Pat. No. 4,589,126, issued May 13, 1986.

In radiotherapy, for example, it is often necessary to provide a relatively large amount of vertical displacement for a patient support table so that a patient may be conveniently placed on the table top near the ground and elevated for treatment to the height of the isocentre of the treatment apparatus which in the case of some forms of high energy source can be high enough to require an under-floor pit 2–3 m deep if a hydraulic ram lift is employed to raise the table top.

The above mentioned EPA 151910 illustrates as an alternative the use of a pair of hollow vertical supporting columns rigidly attached to a mobile base and located on either side of the patient table top. A respective carriage is displaced vertically within each column by means of a nut and threaded shaft drive, and is attached to a corresponding side of the table top by means of a bracket which passes through a corresponding slot in the surface of the column.

This arrangement has certain disadvantages. The use of two pillars, one on either side of the table top, obstructs access both by and to the patient, and it would be more convenient if only one pillar were present enabling freedom of access from one side of the table top. However, a box section pillar whose cross-section is interrupted at one side by a slot discontinuity over the greater part of the height of the pillar, as indicated in EPA 151910, will have insufficient torsional rigidity to support a patient support table top on its own with the positional accuracy and stability required for radiotherapy.

It is an object of the invention to provide an improved radiology patient support system whereby a patient support table top can be firmly and accurately located at an adjustable height by means of a single supporting side pillar.

SUMMARY OF THE INVENTION

According to the invention there is provided a radiology patient support system for radiography, radiotherapy and treatment simulation, including a fundamental support, a patient support table top mounted on a vertically displaceable carriage, and box section vertical supporting pillar means mounted on the fundamental support and provided with guide means and lifting means arranged to support, locate and vertically displace the vertically displaceable carriage, characterised in that the box section vertical supporting pillar means is formed by a single pillar of rigid closed box construction such that the side walls thereof form a closed cross section at substantially all locations along its length, and the guide means is formed by two longitudinal guide tracks adjacently situated with lateral directions at a mutual angle, preferably a right angle, to one another on a supporting surface having a correspondingly angled open V-shaped transverse section which can be rigidly connected to the vertical supporting pillar or can form an outer wall portion of the pillar, the vertically displaceable carriage being provided with bearing members which engage the respective longitudinal guide tracks so as to locate and support the carriage in a vertically displaceable manner relative to the pillar.

The vertically displaceable carriage is preferably also of a rigid closed box construction. One of more transverse plates in the form of intermediate bulkhead walls can be provided at intervals along the length of the pillar, if desired, in order to further increase the torsional stiffness thereof. The longitudinal guide tracks can each be formed as a linear recess between the facing sides of a pair of parallel strips or by a single strip with a bearing surface on each side, the carriage having upper and lower journaled bearing rollers to engage the bearing surfaces of each track. The lifting means for the carriage can comprise a screw threaded shaft mounted in a thrust bearing supported by the pillar, which engages a nut attached to the carriage. Preferably the supports for the thrust bearing and the nut form a cardanic assembly.

Embodiments of the invention will now be described by way of example, with reference to the accompanying drawings of which:

DESCRIPTION OF THE PREFERRED EMBODIMENTS

Figure 1:
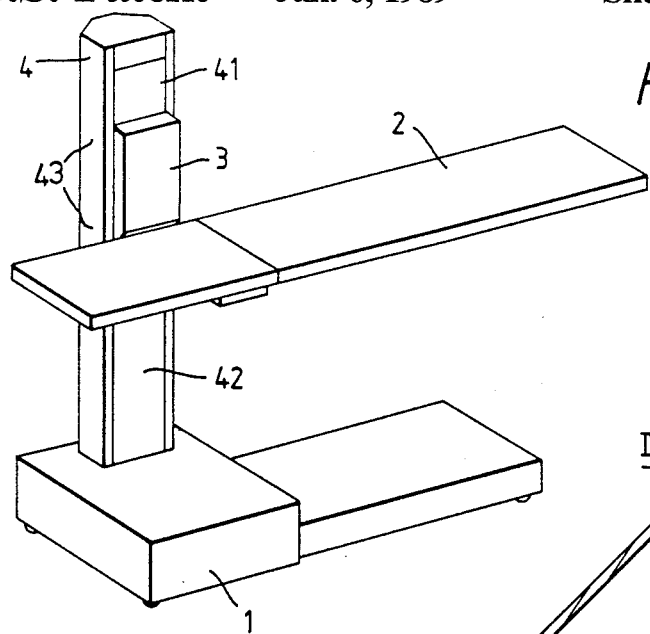
FIG. 1 illustrates diagrammatically a radiology patient support system in accordance with the invention.

FIG. 1 illustrates diagrammatically a radiology patient support system for radiotherapy in accordance with the invention and which includes a fundamental supporting base 1 which can take the form of a mobile trolley as described in EPA 151910. The system can alternatively be mounted directly on the floor, for example by means of a floor mounted turntable as illustrated in EPA 174460. A patient support table top 2 is mounted on a carriage 3 which is vertically displaceable on box section vertical supporting pillar means 4 attached to the base 1.

Figure 2:
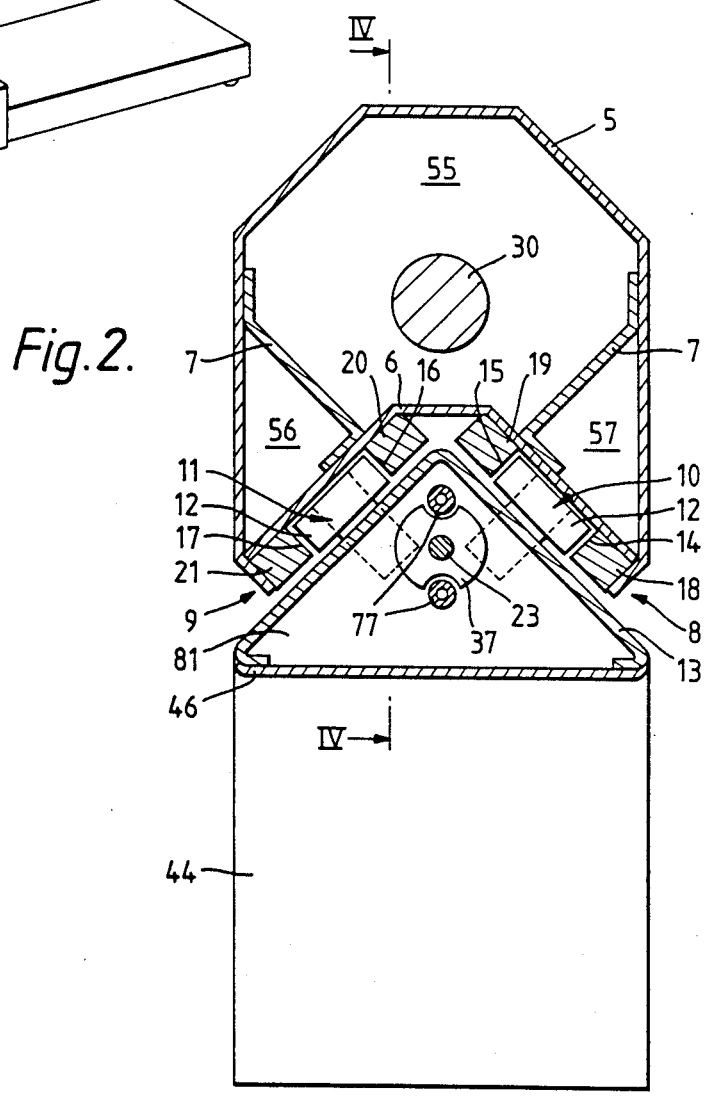
FIG. 2 is a cross sectional view of an embodiment relating to FIG. 1.

In accordance with the invention the vertical supporting pillar means 4 is formed as a single pillar of rigid closed box construction such that the side walls 5, 6, 7, suitably of sheet steel hole welded together and as illustrated with respect to a first embodiment in the cross sectional view of FIG. 2, form a closed cross-section at substantially all locations along the length of the pillar 4. In order to locate the carriage 3 horizontally, the pillar 4 is provided with guide means formed by two longitudinal guide tracks 8, 9 situated adjacent one another with lateral directions at a mutual angle, preferably at right angles, on the supporting outer wall surface 6 which has a generally V-shaped transverse section.

Figure 3:
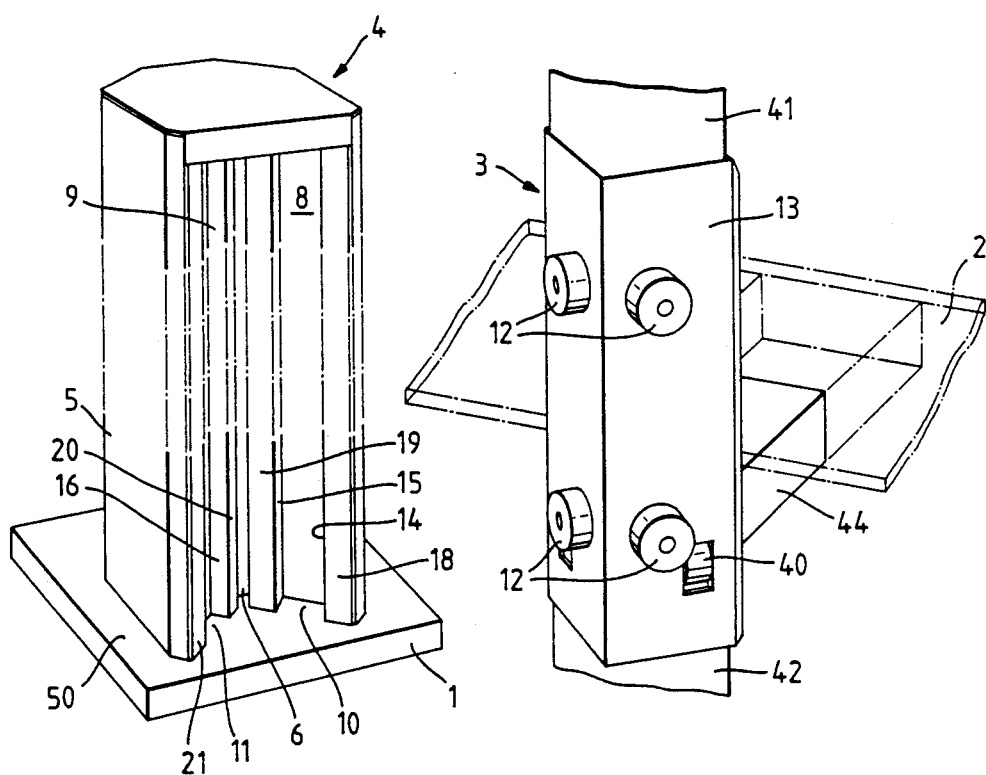
FIG. 3 is a diassembled perspective diagram illustrating the pillar and carriage relating to FIG. 2.

Referring to the first embodiment illustrated in a disassembled perspective view of the pillar 4 and the carriage 3 shown in FIG. 3 and in the cross-section in FIG. 2 relating to the assembled operational system, each guide track 8, 9 of the present embodiment comprises a linear recess 10, 11 formed between a pair of facing bearing surfaces 14, 15 and 16, 17 situated on the corresponding sides of parallel pairs of steel strips 18, 19 and 20, 21 firmly fixed to the wall 6. The vertically displaceable carriage 3 is provided on the outer side of a corresponding V-shaped wall surface 13 with bearing members in the form of rollers 12 which, in operation, are situated in the corresponding recesses 10, 11 so as to engage the respective pairs of facing side faces 14, 15 and 16, 17, thus locating and horizontally supporting the carriage 3 in a vertically displaceable manner relative to the pillar 4. Further horizontal support is provided by rollers 40 which bear on the outer surface of the respective outer strips 18, 21, and are arranged to prevent frictional contact between that face of the wall surface 13 or the end face of the corresponding rollers 20 and the surface of the strips 18, 19 or 20, 21 and of the wall 6.

Figure 4:
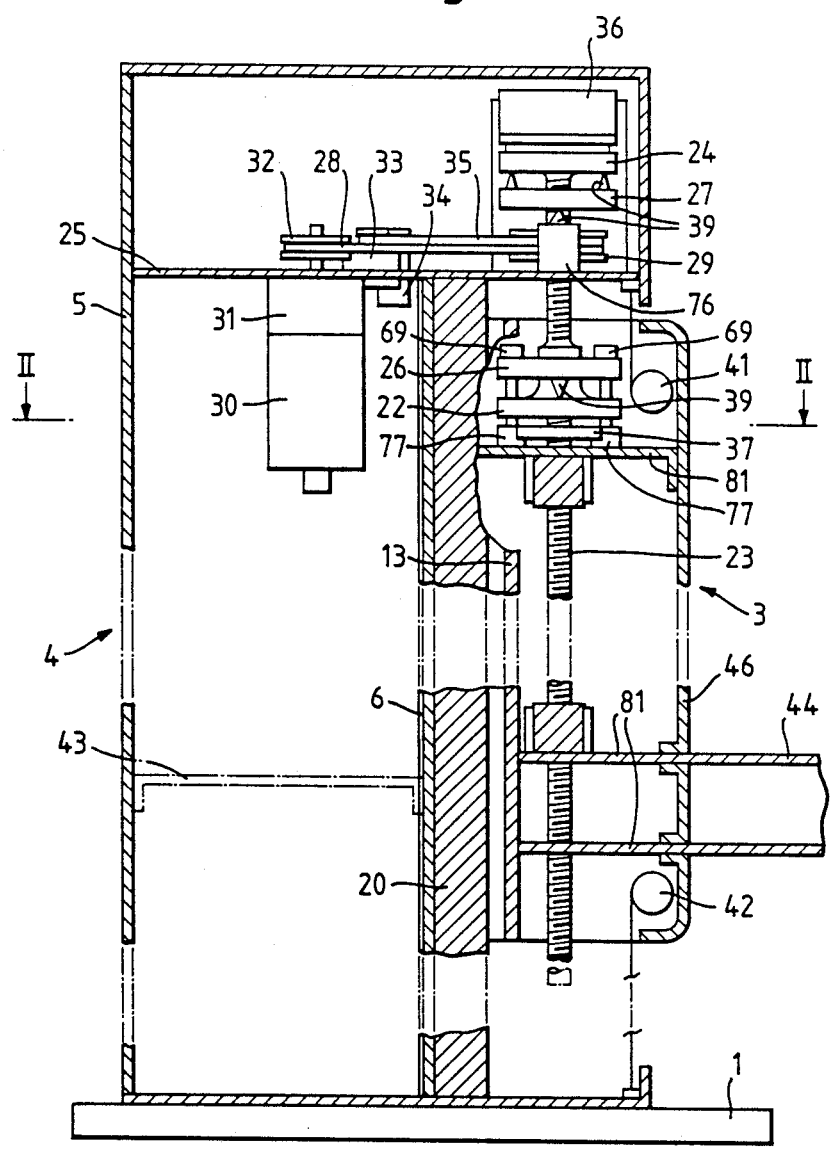
FIG. 4 is an elevation partially in section with some portions cut away, relating to part of the system of FIG. 1.

Referring to FIG. 4, the carriage 3 is located and displaced in a vertical direction by means of a nut 22 connected to the carriage 3, which engages a rotatable screw threaded shaft 23 supported in a thrust bearing 24 mounted on a supporting plate 25 forming an upper bulkhead of the box pillar 4. The threaded shaft 23 is driven via a toothed belt 28 which engages a toothed pinion 29 mounted on the shaft 23, and a further toothed pinion 32 on the output shaft of the reduction gear train 31 of a drive motor assembly 30. Rotation of the shaft 23 and hence the height of the table top 2, is sensed by an angular position sensor 33 and an angular velocity sensor 34 and these are driven by a further toothed belt 35 which also engages the toothed pinion 29 on the shaft 23. A fail-safe brake 36 is fixed to the end of the shaft 23 to hold the vertical table position steady and an idler safety nut 37 is arranged under the nut 22 to operate normally under no-load conditions to act as a safety stop if the thread of the support nut 22 should fail or when a low friction recirculating ball arrangement is used, if the ball cage should burst.

In order to allow for variations in alignment between the supports of the nut 22, the thrust bearing 24 and the threaded shaft 23 as the carriage 3 is displaced vertically on the pillar 4, the nut 22 and the thrust bearing 24 are respectively attached to the carriage 3 and to the supporting plate 25, by a cardanic assembly formed by intermediate suspension plates 26 and 27, respectively. Two pillars 76 located on the supporting plate 25, are diametrically spaced about the axis of the shaft 23 to support the upper intermediate plate 27 via associated bearing projections 39 so that it can tilt about a corresponding diametric transverse axis through the projections 39. The thrust bearing 24 is connected to the upper intermediate plate 27 by two bearing projections 39 which are diametrically spaced about the axis of the shaft 23 in a further transverse direction at right angles to the first mentioned diametric transverse axis so that the thrust bearing 24 is thereby enabled to tilt both about a transverse axis directed along the further transverse direction and about the first mentioned transverse axis. Two pillars 77 located on a transverse plate 81 forming part of the carriage 3, are diametrically spaced about the axis of the shaft 23 and support the lower intermediate support plate 26 by means of corresponding bolts 69 with resilient washers so that the plate 26 can tilt about a corresponding diametric transverse axis through the points of attachment. A flange on the nut 22 is connected to the plate 26 by two bearing projections 39 similarly diametrically spaced about the shaft 23 in a transverse direction at right angles to that of the bolts 69 to enable the nut to tilt about either transverse direction relative to the carriage 3.

In order to protect and to hide the guide tracks 8, 9 and the threaded shaft 23, a respective roller blind 41, 42 is fitted to the upper and lower surfaces of the carriage 3 to extend to the top and bottom of the pillar 4, respectively. The patient support table top 2 is attached to the carriage 3 by means of a connecting bracket 44 which is provided with a releasable table connection means so that different table tops may be substituted e.g. for radiotherapy and for treatment simulation.

The closed box construction of the pillar 4 in which the circumferentially continuous side walls 5, 6 and 7 are closed at both ends by end walls, namely at the top by the supporting plate 25 and at the base 1 by a corresponding end plate 50, provides the pillar 4 with a good degree of torsional stiffness about the vertical axis. This stiffness can be further increased by providing one or more transverse plates in the form of intermediate bulkhead walls 43, suitably of sheet steel hole welded to the side walls and arranged at intervals along the length of the pillar 4. The walls 43 can, if desired, be provided with suitable apertures to accommodate various services such as electrical cables, or apparatus such as motors, and to reduce the overall weight of the pillar. This also applies to the end walls 25 and 50. Provided that the transverse internal walls extend across the main internal space 55 (se FIG. 2), it is not necessary to bridge the minor cavities 56, 57 although it may be desirable to apply some similar transverse stiffening to the rear surface of the wall 6 to ensure a high degree of torsional and flexural rigidity for the guide tracks 8 and 9.

In a corresponding manner, the carriage 3 is made torsionally stiff about a vertical axis by transverse plates 45 suitably of sheet steel hole welded to the V-shaped wall 13 of similar material and arranged at intervals along the vertical dimension. The plates 45 are suitably arranged to support the bearing shafts of the rollers 12 although further transverse plates can be provided intermediately or at either end of the carriage 3. Preferably the front wall 46 of the carriage 3 is also hole welded to the remaining walls to form a closed box construction of good torsional rigidity.

In the embodiment as illustrated in FIGS. 2 and 3, horizontal location of the carriage 3 is provided by using a single upper and lower roller 12 in each respective guide recess 10, 11 on either side of the carriage 3. This means that the spacing of the facing bearing surfaces 14, 15 and 16, 17 must be slightly greater than the diameter of the roller 12 because when the carriage is displaced vertically and the weight distribution urges one side of a roller against one of the bearing surfaces so that the roller turns on its axis, the other side of the roller will move relative to the other bearing surface and if the roller were also in contact with the other surface, friction would be present, rotation of the roller would be inhibited and as a worst case the vertical displacement would jam.

Figure 5:
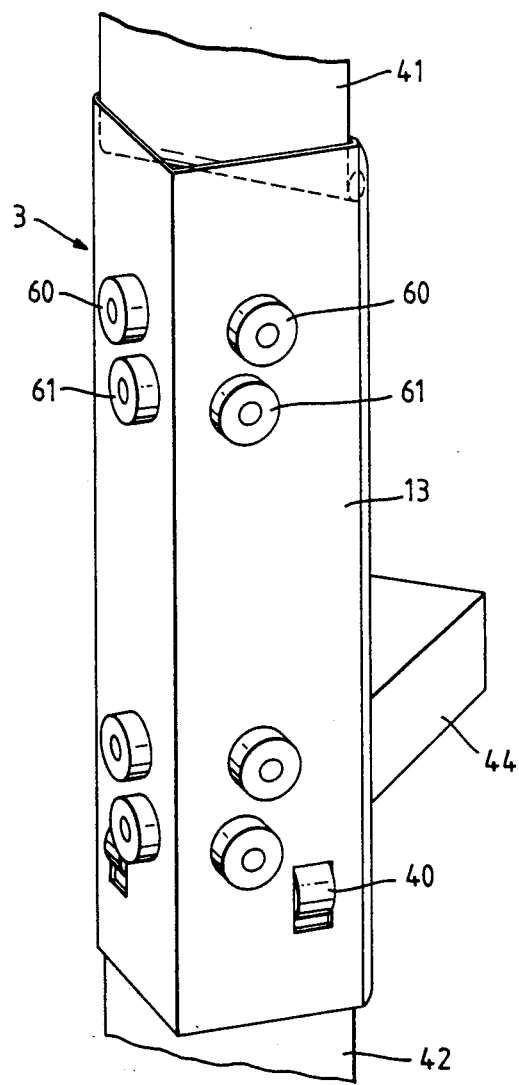
FIG. 5 is a perspective view of an alternative form of carriage relating to FIG. 3.

To overcome this possibility, each roller 12 may be replaced in a modification of this embodiment as illustrated in FIG. 5, by a pair of rollers 60, 61 each of a diameter smaller than the spacing between the facing bearing surfaces. In this arrangement one roller of each pair, namely the horizontal load-bearing roller, is arranged on a fixed mounting on the carriage 3 for accurate horizontal positioning of the carriage 3 and hence of the table top 2, while the other roller of the pair can be mounted on the carriage 3 using a spring pre-loaded horizontally displaceable mount so that the roller is urged into contact with the other bearing surface with a force which effectively prevents horizontal free play across the track and takes up the effect of any small variation along the track of the spacing between the bearing surfaces 14, 15 or 16, 17. With the table top in position as illustrated in FIG. 1, a horizontal load would be applied to the roller nearest the table and to the roller furthest from the table of the respective upper and lower pairs of rollers with respect to the track 8 nearest the main extension and weight of the table, i.e. to the right as shown in FIG. 1 and in the reverse order with respect to the guide track 9 on the other side of the pillar 4. This is because the patient support table top 2 must be supported at one end to enable as much of the length of the table as possible to be introduced into the radiotherapy treatment region which must not contain the vertical support. If it were required to locate the pillar on the other side of the table the loading on the rollers would of course be reversed.

Figure 6:
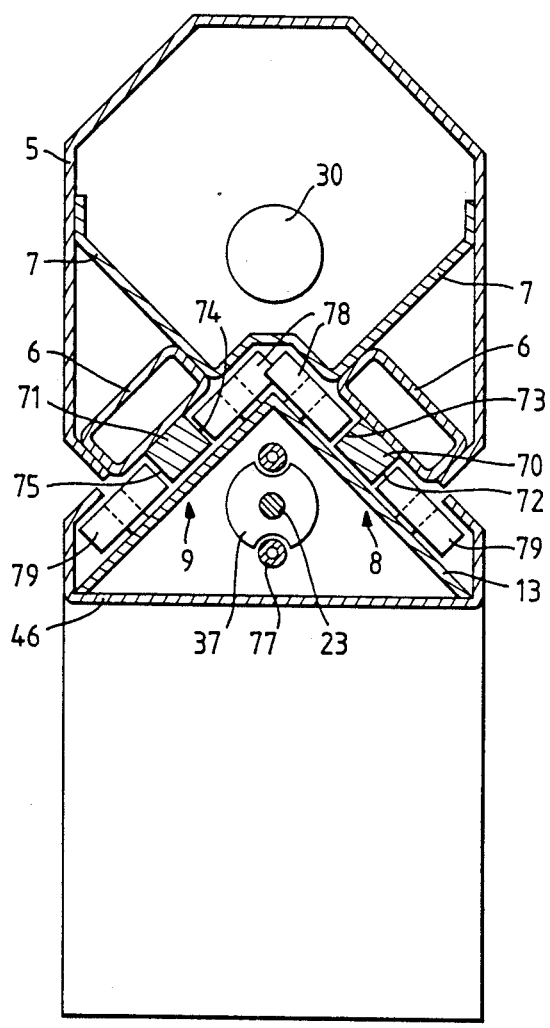
FIG. 6 is a cross sectional view of an alternative embodiment relating to FIG. 1.
Figure 7:
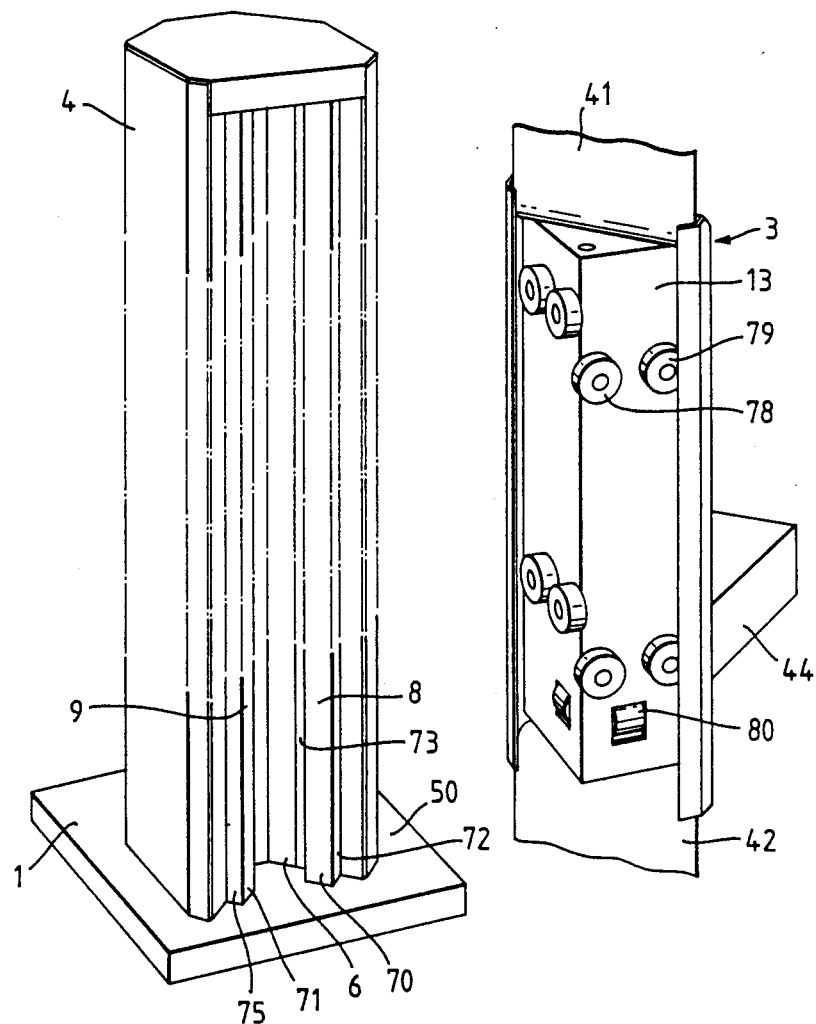
FIG. 7 is a disassembled perspective diagram illustrating the pillar and carriage relating to the embodiment of FIG. 6.

An alternative embodiment of the invention is illustrated in cross-section in FIG. 6 and in a disassembled perspective view of the pillar 4 and the carriage 3 in FIG. 7. In this embodiment each guide track 8, 9 comprises a steel strip 70, 71 whose flat, parallel side surfaces 73, 74 and 72, 75 form inner and outer bearing surfaces, respectively. Each strip 70, 71 is firmly fixed to a corresponding portion of the V-shaped wall 6 of the pillar 4, suitably by hole welding. The vertically displaceable carriage 3 is provided on the outer side of the V-shaped wall surface 13 at respective upper and lower supporting locations, with pairs of rollers each pair comprising an inner roller 78 and an outer roller 79 which in operation respectively engage the corresponding inner and outer bearing surfaces 73, 74 and 72, 75 of the strips 70 and 71. As in the arrangement illustrated in FIG. 5, the load bearing rollers are fixedly mounted on the carriage 3 and the others are spring pre-loaded to avoid free play. In this case, and referring to the table arrangement of FIG. 1, the load bearing rollers on the right would be the inner upper 78 and the outer lower 79 and on the left, the outer upper 79 and the inner lower 78. A corresponding further horizontal support roller 89 is provided one each side to bear on the top surface of each strip 70, 71 to serve the same function as that of the rollers 40 shown in FIG. 3.

While the arrangements shown in FIGS. 2, 3, 5 and 6, 7 have been described as relating to different embodiments, it is nevertheless possible, if desired to form one of the guide tracks of a patient support system in accordance with the invention, in accordance with one of the arrangements and to form the other in the other way. This could be desirable since the loading applied to the two tracks is different because of the need to support the table top at one end.

What is claimed is:

1. Radiology patient support system for radiography, radiotherapy or treatment simulation, including a fundamental support, a patient support table top mounted on a vertically displaceable carriage, and box section vertical supporting pillar means mounted on the fundamental support and provided with guide means and lifting means arranged to support, locate and vertically displace the vertically displaceable carriage, wherein the box section vertical supporting pillar means is formed by a single pillar of rigid closed box construction such that the side walls thereof form a closed cross section at substantially all locations along its length, and the guide means is formed by two longitudinal guide tracks adjacently situated with lateral directions at a mutual angle to one another on a supporting surface having a correspondingly angled open V-shaped transverse section, which is rigidly connected to the pillar, the vertically displaceable carriage being provided with bearing members which engage the respective longitudinal guide tracks so as to locate and support the carriage in a vertically displaceable manner relative to the pillar.

2. The radiology patient support system as claimed in claim 1 wherein the mutual angle between the lateral directions of the longitudinal guide tracks is a right angle.

3. The radiology patient support system as claimed in claim 1 or claim 2 wherein the V-shaped supporting surface forms an outer wall portion of the pillar.

4. The radiology patient support system as claimed in claim 1 or claim 2 wherein the vertically displaceable carriage is of a rigid closed box construction.

5. The radiology patient support system as claimed in claim 1 or claim 2 wherein a plurality of transverse plates are provided along the length of the pillar in order to increase the torsional stiffness.

6. The radiology patient support system as claimed in claim 1 or claim 2 wherein at least one of the longitudinal guide tracks is a corresponding linear recess formed between a pair of facing parallel bearing surfaces, and the bearing members associated with that track comprise at least two journaled bearing rollers mounted on the vertically displaceable carriage in vertically spaced relationships.

7. The radiology patient support system as claimed in claim 1 or claim 2 wherein at least one of the longitudinal guide tracks is formed by a corresponding raised longitudinal guide member whose side faces are parallel, and the bearing members associated with that track comprise two pairs of journalled bearing rollers mounted on the vertically displaceable carriage in vertically spaced relationship, the rollers of each pair being located one on each side of the guide member so as to engage the corresponding side face thereof.

8. The radiology patient support system as claimed in claim 1 or claim 2 wherein the lifting means comprise a rotatable screw threaded shaft mounted in a thrust bearing mounted on the vertical supporting pillar and engaging a nut attached to the vertically displaceable carriage.

9. The radiology patient support system as claimed in claim 8 wherein the thrust bearing and the nut are pivotally attached to the pillar and to the carriage, respectively, so as to form a cardanic assembly.

* * * * *